(12) United States Patent
Bates

(10) Patent No.: US 7,973,929 B2
(45) Date of Patent: Jul. 5, 2011

(54) SYSTEM AND METHOD FOR CALIBRATION VERIFICATION OF AN OPTICAL PARTICLE COUNTER

(75) Inventor: Thomas Bates, Westminster, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 196 days.

(21) Appl. No.: 12/271,565

(22) Filed: Nov. 14, 2008

(65) Prior Publication Data

US 2009/0128810 A1   May 21, 2009

Related U.S. Application Data

(60) Provisional application No. 60/988,515, filed on Nov. 16, 2007.

(51) Int. Cl.
*G01N 15/02* (2006.01)

(52) U.S. Cl. ............................ 356/336; 356/338; 377/10

(58) Field of Classification Search .......... 356/335–343, 356/243.1–243.8; 377/10–11
See application file for complete search history.

(56) References Cited

U.S. PATENT DOCUMENTS

| | | | |
|---|---|---|---|
| 3,851,169 A | 11/1974 | Faxvog | |
| 4,348,111 A | 9/1982 | Goulas et al. | |
| 4,360,270 A | 11/1982 | Jeck | |
| 4,434,647 A | 3/1984 | Whitcomb et al. | |
| 4,728,190 A | 3/1988 | Knollenberg | |
| 4,957,363 A | 9/1990 | Takeda et al. | |
| 5,059,395 A | * 10/1991 | Brittenham et al. | ............ 422/73 |
| 5,085,500 A | 2/1992 | Blesener | |
| 5,121,988 A | 6/1992 | Blesener et al. | |
| 5,467,188 A | 11/1995 | Miyashita | |
| 5,642,193 A | 6/1997 | Girvin et al. | |
| 5,684,585 A | 11/1997 | Girvin | |
| 5,747,667 A | 5/1998 | Sadar | |
| 5,864,399 A | 1/1999 | Girvin et al. | |
| 5,912,737 A | 6/1999 | Bannerjee et al. | |
| 5,920,388 A | 7/1999 | Sandberg et al. | |
| 5,946,092 A | 8/1999 | DeFreez et al. | |
| 6,639,670 B2 | 10/2003 | Carpenter | |
| 6,859,277 B2 | 2/2005 | Wagner et al. | |
| 6,883,516 B2 | 4/2005 | Hindle et al. | |
| 7,030,980 B1 | 4/2006 | Sehler et al. | |

(Continued)

FOREIGN PATENT DOCUMENTS

WO   WO 2006/067371   6/2006

OTHER PUBLICATIONS

ASTM E1458-92(2001) (2001) Standard Test Methods for Calibration Verification of laser Diffraction Particle Sizing Instruments Using Photomask Reticles.

(Continued)

*Primary Examiner* — Hoa Q Pham
(74) *Attorney, Agent, or Firm* — Greenlee Sullivan P.C.

(57) ABSTRACT

Described herein is a portable, low power consuming optical particle counter calibration verification system and reliable and sensitive methods for verifying the calibration status of a gas or liquid particle counter. The calibration verification systems described herein are useful for quickly determining the calibration status of an optical particle counter at its point of use, as well as for allowing the end user to determine if an optical particle counter is in need of a recalibration before the recommended calibration schedule suggests.

38 Claims, 9 Drawing Sheets

U.S. PATENT DOCUMENTS

| | | | |
|---|---|---|---|
| 7,053,783 | B2 | 5/2006 | Hamburger et al. |
| 7,928,718 | B2 * | 4/2011 | Larsen .................. 324/71.4 |
| 2006/0198940 | A1 | 9/2006 | McMorrow |
| 2007/0013910 | A1 * | 1/2007 | Jiang et al. ............ 356/336 |
| 2007/0197486 | A1 | 8/2007 | Hill |
| 2007/0200548 | A1 * | 8/2007 | Petersen et al. ......... 324/76.16 |
| 2008/0208511 | A1 * | 8/2008 | Trainer ................. 702/128 |

OTHER PUBLICATIONS

ASTM F328-98: Standard Practice for Calibrating an Airborne Particle Counter Using Monodisperse Spherical Particles, 2003.

Dhand, R. (2003) "New Nebuliser Technology—Aerosol Generation by Using a Vibrating Mesh of Plate with Multiple Apertures," Business Briefing: Long Term Healthcare Strategies.

International Search Report and Written Opinion Corresponding to International Application No. PCT/US2008/083669, Mailed Jan. 16, 2009.

ISO/FDIS 21501-4 Determination of Particle Size Distribution—Single Particle Light Interaction Methods—Part 4: Light Scattering Airborne Particle Counter for Clean Spaces, 2007.

JIS B 9921: Light Scattering Automatic Particle Counter, *Japanese Industrial Standard*, 1997.

Met One Instruments, Jan. 1990, "Laser Particle Counters," Operating Guide.

Met One Instruments "E-Bam" Product Brochure, Unknown Publication Date, http://www.metone.com/documents/E-BAM_Brochure.pdf.

Omron, (2003) Instruction Manual, Micro Air Vibrating Mesh Nebulizer Models NE-U22V and NE-U22VAC.

* cited by examiner

SYSTEM AND METHOD FOR CALIBRATION VERIFICATION OF AN OPTICAL PARTICLE COUNTER

CROSS REFERENCE TO RELATED APPLICATION

This application claims priority under 35 U.S.C. §119(e) to U.S. Provisional Patent Application No. 60/988,515 filed on Nov. 16, 2007, which is hereby incorporated by reference in its entirety.

STATEMENT REGARDING FEDERALLY SPONSORED RESEARCH OR DEVELOPMENT

Not Applicable.

BACKGROUND OF THE INVENTION

This invention is in the field of optical particle counters. This invention relates generally to calibration verification systems and methods for verifying the calibration status and performance of optical particle counters.

A large portion of the micro-contamination industry is reliant on the use of optical particle counters, such as are described in a large number of U.S. patents, including U.S. Pat. Nos. 3,851,169, 4,348,111, 4,957,363, 5,085,500, 5,121,988, 5,467,188, 5,642,193, 5,864,399, 5,920,388, 5,946,092, and 7,053,783. U.S. Pat. Nos. 4,728,190, 6,859,277, and 7,030,980, also disclose optical particle counters and are hereby incorporated by reference in their entirety. Aerosol optical particle counters are used to measure air-born particle contamination in clean-rooms and clean zones. Liquid particle counters are often used to optically measure particulate contamination in the water treatment and chemical processing industries.

Optical particle counters for these applications generally have one year calibration cycles. International standards such as JIS B 9921: *Light Scattering Automatic Particle Counter*, ASTM F328-98: *Standard Practice for Calibrating an Airborne Particle Counter Using Monodiperse Spherical Particles*, and ISO/FDIS 21501-4: *Determination of particle size distribution—Single particle light interaction methods—Part 4: Light scattering airborne particle counter for clean spaces* are available that detail the calibration requirements for optical particle counters.

The calibration process for an optical particle counter is complicated and usually requires trained representatives from the particle counter manufacturer to perform the calibration. The calibration process is centered on the use of certified particle size standards. In the United States, these standards are water suspended polystyrene spheres, traceable to the National Institute of Standards and Technology (NIST). A typical particle generation system for providing calibration standard particles to an aerosol optical particle counter is exemplified as a Model PG-100 Particle Generator 100, as shown in FIG. 1.

In reference to FIG. 1, air is pulled into the system at position 101 by means of a pump 102. This air is filtered 103 to remove any particles in the flow. As the calibration standard particles are water suspended, they must be aerosolized by a particle generator for detection by an aerosol optical particle counter. The water and particle mixture is placed into a nebulizer 104 where it is aerosolized by the nebulizer with a stream of pressurized air produced by the particle generator pump. Valve 105 regulates the flow rate through the nebulizer 104. The particle generator pump 102 is typically large, heavy, and power consuming, generally requiring AC power. The air and water mist (water droplets that contain polystyrene spheres) from the nebulizer is then combined with any residual airflow from the particle generator pump 102 through bypass valve 106 and passed through one or more drying chambers 107 and 108 in order to allow the evaporation of the water droplets. Once the water droplets have evaporated, only the polystyrene spheres remain in the particle generator air flow. As shown in FIG. 2, the particle air flow is then combined with a larger filtered air flow provided by a filter-tee assembly 109 in order to provide the particle counter (exemplified in FIG. 2 as a LASAIR Model particle counter 110) with the full amount of its required air flow.

In this manner, mono-dispersed particles of known sizes are used to calibrate each corresponding particle channel of the particle counter. For example; a 1.0 µm particle is used to calibrate a 1.0 µm channel. This ensures that each particle channel of the unit under test sizes particles accurately.

In addition to the testing described above, it is also generally required to inter-compare the test instrument with a reference particle counter. This is done, for example, to ensure the test instrument achieves 50% counting efficiency at its stated first channel particle size, and 100% counting efficiency at 1.5 to 2.0 times its stated first channel particle size. Comparison testing requires an entirely different flow system in addition to the one shown in FIG. 2 in order to ensure a homogenous mixture of filtered air and particles is delivered to both the unit under test and the reference instrument.

It is generally also required to measure and confirm the flow rate of the unit under test with a NIST traceable flow meter, as well as to perform a zero-count (false count rate) test. For some application, the instrument is generally required to demonstrate an achievable false count rate of less than one count in five minutes with a 95% upper confidence limit. This test is very time consuming and may require an extended total sampling time of over an hour.

A full optical particle counter calibration is complicated and, thus, generally must be performed by a trained representative from the particle counter manufacturer. A full calibration typically requires a large amount of test equipment which is not portable. Generally, the optical particle counter under test must be brought to the calibration equipment location.

For cost reasons and ease of implementation, particle counter users generally limit calibration to a one year calibration cycle, as typically recommended by particle counter manufacturers. The industry range for aerosol particle counter calibrations is $300 to $1200, per instrument, per calibration. Particle counter users must assume that the particle counter will maintain proper calibration throughout the one year calibration cycle, although this is sometimes not the case.

Aerosol particle counter users are segmented into a number of industries. For example, the semiconductor and pharmaceutical industries are two industries for which particle measuring plays a significant role. Semiconductor users generally monitor aerosol contamination in order to improve or maintain wafer yield levels. If an aerosol optical particle counter drifts out of calibration in one of these clean areas, the particle counter may over- or under-count the particle level in the clean area. If the particle counter is under-counting, the clean area may be dirtier than the user believes. In a worst case scenario, the user may experience a drop off in wafer yield due to this undetected particle contamination. While the drop off in yield is undesirable, the user is at least given real time feed-back from quality control monitoring of the wafer yield, and will have some stimulation to investigate a possible problem within that specific clean area. Ultimately, the out of calibration particle counter would be revealed as the reason for the drop off in wafer yield.

An out of calibration particle counter also presents significant problems to a pharmaceutical user. Pharmaceutical users must monitor clean areas where pharmaceuticals are handled or processed. In the United States, this monitoring is mandated by the Food and Drug Administration (FDA). The process areas must be maintained to a specified cleanliness level established for certain pharmaceutical products. If a particle counter is under-counting, the clean process area may be dirtier than the user believes. The user has no means of detecting the out of calibration particle counter, as there is no real time feed-back of any process that would indicate a problem. The user may continue to process pharmaceuticals in the suspect clean area for the remainder of the annual calibration cycle of the particle counter, before finally being informed that the particle counter was out of calibration upon its next scheduled calibration.

As liquid particle counters are often used to optically measure particulate contamination in purified water and chemical streams, when a liquid particle counter is under-counting, the water or chemical streams may include particulate levels higher than a user believes. For example, if a liquid source includes particle levels higher than expected, this may result in an end product, of which this liquid which is a component, having contamination levels higher than expected. As above, this may pose a significant problem, for example if the end product is a pharmaceutical composition. Alternatively, if the liquid is utilized, for example, as a rinse, wash or solvent during the processing of a semiconductor device, particle contamination of the semiconductor device may result, resulting in decreased semiconductor device yield.

Once the particle counter is defined as out of calibration, the status of the clean area that it monitored for that entire calibration cycle (typically a year) is in question. If it is determined that the particle counter sufficiently under-counted so as to place the actual clean area it monitored above the allowed FDA specified contamination limit, all product produced in that area for the entire year becomes suspect. The user may be forced to recall the entire year's pharmaceutical product produced in the suspect area. This is a disaster that could cost the pharmaceutical user millions of dollars in lost product.

Calibration systems and methods for evaluating the calibration status of optical particle counters can be found in U.S. Pat. Nos. 4,360,270, 4,434,647, and 5,684,585. U.S. Pat. No. 4,360,270 discloses passing thin, translucent fibers through the laser of an optical particle counter to give a fixed, repeatable signal useful for determination of calibration status of the optical particle counter. Similarly, U.S. Pat. No. 4,434,647 discloses passing a probe with an opaque, precisely sized circular spot through the laser of an optical particle counter. U.S. Pat. No. 5,684,585 discloses modulation of the laser beam intensity to simulate the detection of particles of a known size. These particle-type events may be compared to those previously determined when the particle counter was known to be properly calibrated to verify if the particle counter remains properly calibrated. The primary drawback to these and similar methods and systems is that they do not employ actual particles for testing the optical particle counter. Use of particles similar to those used during calibration is beneficial for ensuring that the calibration verification can be relied upon as an accurate measure of the continued calibration (or identified mis-calibration) of the particle counter.

Other methods are known for the calibration verification of a particle counter, such as described in U.S. Pat. No. 5,747,667. This patent discloses passing a known number of particles through a particle counter and comparing with the actual number of particles detected. Although this method is useful and uses standardized particles, it appears to only consider counting accuracy and is practical only for particle counters which measure particles suspended in a liquid. Optical particle counters may become mis-calibrated for a number of reasons including drift in the detection electronics; such a mis-calibrated particle counter may still properly count the total number of particles but may misidentify the real sizes of particles.

SUMMARY OF THE INVENTION

Described herein is a portable, low power consuming optical particle counter calibration verification system and reliable and sensitive methods for verifying the calibration status of a gas or liquid particle counter. The calibration verification systems described herein are useful for quickly determining the calibration status of an optical particle counter at its point of use, as well as for allowing the end user to determine if an optical particle counter is in need of a recalibration before the recommended calibration schedule suggests.

In an embodiment, the calibration verification system is incorporated into an optical particle counter. In another embodiment, the calibration verification system is distinct from the optical particle counter. Both of these embodiments are useful with the methods described herein for verifying the calibration status of the optical particle counter.

In an embodiment, a method for verifying the calibration status of an optical particle counter comprises the steps of: providing an optical particle counter; transporting particles having a preselected size distribution through the optical particle counter; measuring a pulse height distribution of the particles with a preselected size distribution; analyzing the pulse height distribution by determining a calibration verification parameter or set of calibration verification parameters; and comparing the calibration verification parameter or set of calibration verification parameters with one or more reference values, thereby verifying the calibration status of an optical particle counter.

In an embodiment, a method of this aspect may further comprise the step of indicating the calibration status of the optical particle counter to a user. In another embodiment, a method of this aspect may further comprise the step of storing the calibration verification parameter or set of calibration verification parameters or one or more reference values in a memory system of the optical particle counter for later retrieval, comparison, or other use.

In an embodiment, useful calibration verification and/or reference parameters include, but are not limited to: a median value of the pulse height distribution for the particles having a preselected size distribution; a width of the pulse height distribution for the particles having a preselected size distribution; a slope of the noise floor of the optical particle counter; a zero count failure point of the optical particle counter; a signal-to-noise ratio equal to the ratio of the median value of the pulse height distribution and the zero count failure point for the optical particle counter; and any combination of these.

In an embodiment, useful reference values are calibration verification parameters predetermined for a pre-calibrated or reference optical particle counter. In an embodiment, useful reference values are calibration verification parameters previously determined for the same optical particle counter under evaluation but in a known positive-calibration state. In an embodiment, useful reference values are stored in and/or retrieved from a memory system of the optical particle counter or calibration verification system.

In an embodiment, the calibration verification parameter or set of parameters are compared with reference values. In an embodiment, the comparison comprises comparing a median value of the measured pulse height distribution of particles having a predetermined size distribution with a reference pulse height distribution median value. In an embodiment, an indication is provided to the user that the optical particle counter has a positive calibration status if the measured pulse height distribution median value is within 10%, or in some embodiments within 25%, of the reference pulse height distribution median value. In an embodiment, an indication is provided to the user that the optical particle counter has a negative calibration status if the measured pulse height distribution median value is greater than 110% or less than 90%, or in some embodiments greater than 125% or less than 75%, of the reference pulse height distribution median value.

In another embodiment, the comparison comprises comparing a width of the measured pulse height distribution of particles having a predetermined size distribution with a reference pulse height distribution width. In an embodiment, an indication is provided to the user that the optical particle counter has a positive calibration status if the measured pulse height distribution width is within 15%, within 5% in some embodiments, or within 25% in other embodiments, of the reference pulse height distribution width. In an embodiment, an indication is provided to the user that the optical particle counter has a negative calibration status if the measured pulse height distribution width is greater than 115% or less than 85%, in some embodiments greater than 105% or less than 95%, or in other embodiments greater than 125% or less than 75%, of the reference pulse height distribution width.

In an embodiment, the particle counter undergoing calibration verification is tested under conditions where no particles are present in the particle counter. Such conditions are useful for the determination of the particle counter's false count rate. In an embodiment, a series of false count rates are determined for a variety of threshold voltages/pulse heights and fit to a line or curve. Here, the slope of the best fit line (i.e., slope of the noise floor) is useful, for example, in that it allows for extrapolation to larger threshold values where the false count frequency is smaller and an accurate determination of the actual false count rate could take a long time. In an embodiment, the false count rate is prespecified to be a false count rate larger than an acceptable count rate and the extrapolation allows for determination of such a zero count failure point; that is, the threshold voltage at which the prespecified false count rate is expected to fall. In an embodiment, the zero count failure point is equivalent to the particle counter's noise level, and a useful signal to noise ratio can be determined from the ratio of the median of the pulse height distribution for particles having a preselected size distribution to the zero count failure point of the particle counter.

In an embodiment, a comparison useful for a method of this aspect comprises comparing a particle counter's slope of the noise floor with a reference slope of the noise floor. In an embodiment, an indication is provided to the user that the optical particle counter has a positive calibration status if the slope of the noise floor is within 10%, or in some embodiments within 25%, of the reference slope of the noise floor. In an embodiment, an indication is provided to the user that the optical particle counter has a negative calibration status if the slope of the noise floor is greater than 110% or less than 90%, or in some embodiments greater than 125% or less than 75%, of the reference slope of the noise floor.

In another embodiment, the comparison comprises comparing a particle counter's zero count failure point with a reference zero count failure point. In an embodiment, an indication is provided to the user that the optical particle counter has a positive calibration status if the zero count failure point is within 10% or in some embodiments within 25%, of the reference zero count failure point. In an embodiment, an indication is provided to the user that the optical particle counter has a negative calibration status if the zero count failure point is greater than 110% or less than 90%, or in some embodiments greater than 125% or less than 75%, of the reference zero count failure point.

In another embodiment, the comparison comprises comparing a signal-to-noise ratio of the measured pulse height distribution with a reference pulse height distribution signal-to-noise ratio. In an embodiment, an indication is provided to the user that the optical particle counter has a positive calibration status if the measured pulse height distribution signal-to-noise ratio is within 10%, or in some embodiments within 25%, of the reference pulse height distribution signal-to-noise ratio. In an embodiment, an indication is provided to the user that the optical particle counter has a negative calibration status if the measured pulse height distribution signal-to-noise ratio is greater than 110% or less than 90%, or in some embodiments greater than 125% or less than 75%, of the reference pulse height distribution signal-to-noise ratio.

In an embodiment, an indication is provided to the user that the optical particle counter has a negative calibration status if any of the calibration verification parameters are outside of the acceptable ranges for each of the individual calibration verification parameters. In a similar embodiment, an indication is provided to the user that the optical particle counter has a positive calibration status only if all of the calibration verification parameters are within acceptable ranges for each of the individual calibration verification parameters. In an embodiment, the user is provided with information regarding which calibration verification parameters are inside of or outside of acceptable ranges for those calibration verification parameters.

In an embodiment, useful preselected particle size distributions comprise monodisperse distributions. In an embodiment, useful preselected particle size distributions comprise a plurality of monodisperse distributions. In an embodiment, the calibration verification method is performed without removing the particle counter from its operating location. In an embodiment, the calibration verification method is performed in the location where the optical particle counter is installed or operated.

In another aspect, provided herein are systems useful for calibration verification of an optical particle counter. In an embodiment, such a calibration verification system is comprised of: a particle generator for providing particles having a preselected size distribution to an optical particle counter; a pulse height analyzer operably connected to the optical particle counter for measuring a pulse height distribution for the particles having a preselected size distribution; and calibration verification analyzer operably connected to the pulse height analyzer for analyzing the pulse height distribution by determining a calibration verification parameter or set of calibration verification parameters and comparing the calibration verification parameters or set of calibration verification parameters with one or more reference values. In an embodiment, a particle generator useful in the systems of the present invention comprises a vibrating mesh nebulizer.

The methods described herein need not be limited to the calibration verification of an optical particle counter. In an embodiment, a method is exemplified as a business method for verifying the calibration status of an instrument. Such a method comprises the steps of: providing a measuring instrument; providing a calibration standard to the instrument; making a plurality of measurements of the calibration standard with the measuring instrument; analyzing the measurements by determining a calibration verification parameter or set of calibration verification parameters; and comparing the calibration verification parameter or set of calibration verification parameters with one or more reference values, thereby verifying the calibration status of the measuring instrument. In an exemplary embodiment, the measuring instrument is provided at its point of use.

In an embodiment, the calibration verification and/or reference parameters useful in the above exemplified business method for verifying the calibration status of a measuring instrument include, but are not limited to: a median value of the plurality of measurements of the calibration standard; a width of the plurality of measurements of the calibration standard; a zero offset for the measuring instrument; a noise level for the measuring instrument; a signal-to-noise ratio equal to the ratio of the median value of the plurality of measurements to the noise level for the measuring instrument; and any combination of these.

As a further example, the above described business method for verifying the calibration status of an instrument can be useful for measurement or monitoring instruments including, but not limited to optical particle counters; pressure measuring devices; temperature measuring devices; speed measuring devices; distance or length measuring devices; size measuring devices; volume measuring devices; time measuring devices; counters or quantity measuring devices; frequency or repetition rate measuring devices or monitors; devices which measure acceleration; devices which measure concentration; flow rate measuring devices; stress measuring or monitoring devices; strain measuring or monitoring devices; compressibility or compression measuring devices; force, mass, or weight measuring or monitoring devices; devices which measure or monitor electrical properties such as resistance, conductance, current, voltage, charge, capacitance or inductance; devices which measure optical properties such as absorption, extinction, intensity, energy, frequency, or color; and devices which measure acoustic properties such as intensity, volume, pitch, tone, or frequency.

DETAILED DESCRIPTION OF THE INVENTION

Figure 1:
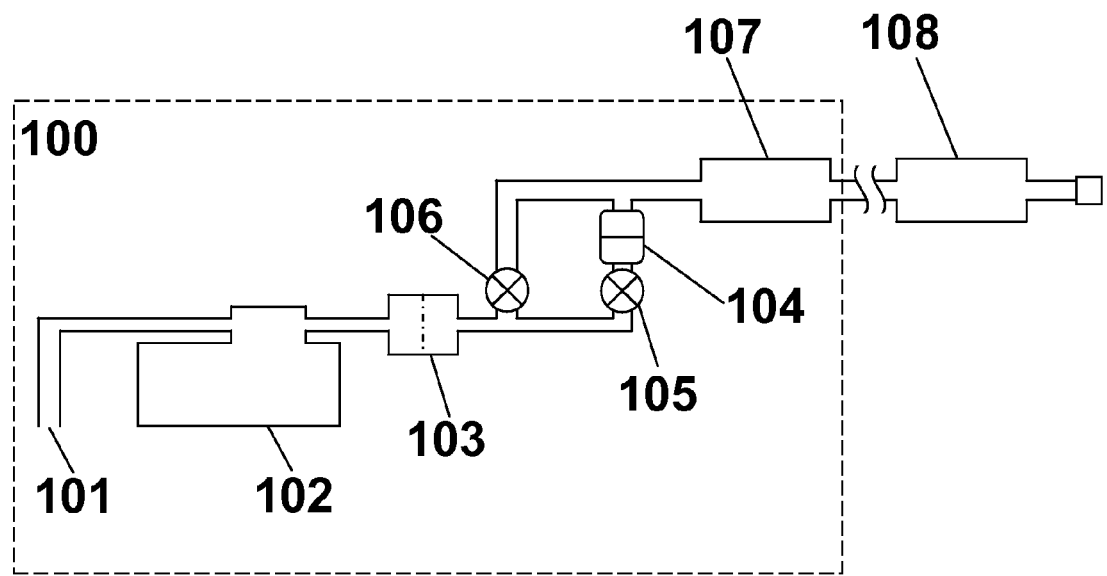
FIG. 1 illustrates a typical particle generation system.
Figure 2:
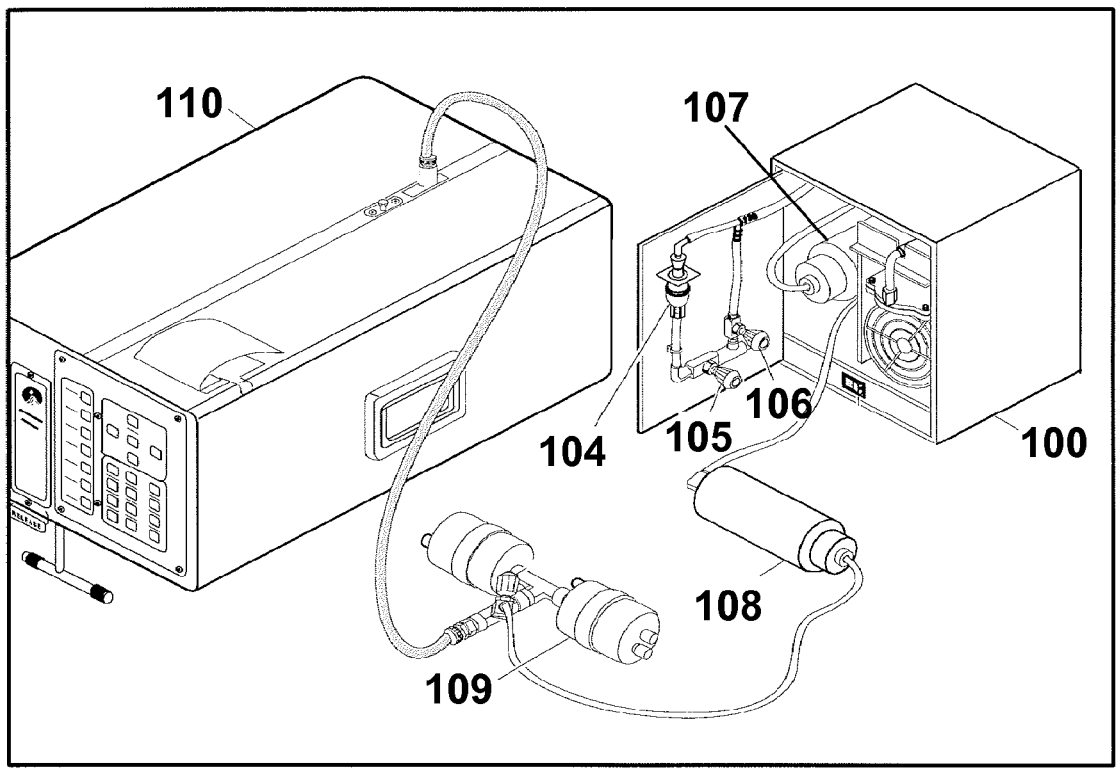
FIG. 2 illustrates a typical calibration system for particle generation.

In general the terms and phrases used herein have their art-recognized meaning, which can be found by reference to standard texts, journal references and contexts known to those skilled in the art. The following definitions are provided to clarify their specific use in the context of the invention.

"Pulse height analyzer" or "PHA" refers to hardware or software used to analyze the height of an input pulse and outputs a signal representative of the height of the input pulse. A "pulse height analyzer" also can refer to hardware or software used to analyze the width, median, or shape of a distribution of input pulses and outputs a signal representative of the width, median, or shape of the distribution. As an example, in an optical particle counter, light scattered off of a particle is detected by a photodetector which outputs a current; a current to voltage converter changes this current to a voltage which may be amplified and then provided to a pulse height analyzer; a pulse height analyzer can then output a signal proportional to the size of a detected particle. A pulse height analyzer can be used to count the number of events of a particular intensity, for example the number and size of particles detected by an optical particle counter. In an embodiment, a pulse height analyzer outputs a signal representative of the height or maximum voltage of a single input pulse. In an embodiment, a pulse height analyzer receives a plurality of input pulses corresponding to scattered electromagnetic radiation from an optical particle counter, for example corresponding to electromagnetic radiation scattered by particles, and outputs a signal representative of the median value of the distribution of input pulses or full width at half maximum, or other width, of the distribution of input pulses. In an exemplary embodiment, a pulse height analyzer is useful for determining the median value and/or width of a distribution of 10000 or more events, 1000 or more events, and in some embodiments 100 or more events. An exemplary pulse height analyzer useful in the methods and systems of the present invention is a Canberra Multiport II Model MP2-2E.

"Pulse height distribution" refers to the distribution of pulses detected by a pulse height analyzer. In an embodiment, a pulse height distribution is the output of a pulse height analyzer. It can be represented in the form of a table where x is the voltage bin and y is the frequency or number of events. It is often presented visually as a histogram plot of the outputs of a pulse height analyzer. The x-axis of a histogram plot of a pulse height distribution is a range of sequential voltage bins, for example 0-10 V. The y-axis of a histogram plot of a pulse height distribution represents the frequency or number of events, for example optical particle detection events. "Pulse height distribution" and "pulse height analyzer" are used interchangeably herein, and can refer to any of the software/hardware performing the pulse height analysis, the actual distribution of pulse heights, the data in a table format, and the histogram plot.

"Median value of a pulse height distribution" refers to a voltage level of a pulse height distribution. Half of the population of a pulse height distribution will fall above the median value and half of the population will fall below the median value.

"Width of a pulse height distribution" refers to the difference between two voltage values of a pulse height distribution. In an embodiment, the width of a pulse height distribution is the standard deviation of the pulse height distribution. In an embodiment, the width of a pulse height distribution is the full width at half of the maximum of the pulse height distribution. In an embodiment, the width of a pulse height distribution is equal to the difference between the voltage values corresponding to an upper and lower count or count rate of a pulse height distribution. In an embodiment, the upper and lower count rates are defined as the count or count rate corresponding to a specific fall off in event activity compared to the median of the distribution, for example a specific count or count rate of 25%, 33%, 50%, or 60% of the median value.

"Slope of the noise floor" refers to the slope of a best fit line to a series of false count rates of an optical particle counter (i.e., count rates determined when no particles are present in the particle counter). Several false count rates are determined for a series of different voltage threshold levels (i.e., pulse heights) and these points are fit to a line and used in an extrapolation to determine the zero count failure point of the particle counter.

"Zero count failure point" refers to the threshold voltage level or pulse height at which a particle counter will detect less than a prespecified number of counts in a specified time period when there are no particles in the particle counter (i.e., false counts). The zero count failure point need not refer to the same false count frequency for all applications. In an embodiment, the zero count failure point refers to the threshold voltage level at which a particle counter will detect less than one count in five minutes (i.e., 0.00333 counts per second) when there are no particles in the particle counter.

"Signal-to-noise ratio" refers to the ratio of the median value of a pulse height distribution measured by a particle counter for particles having a preselected size distribution and the zero count failure point of the optical particle counter.

"Calibrated state" and "Positive calibration status" refers to the state of an optical particle counter which has met or passed all of the selected or desired requirements of the calibration verification system and found to be calibrated. An optical particle counter having a positive calibration status may not need to be recalibrated.

"Negative calibration status" refers to the state of an optical particle counter which has failed one or more of the selected or desired requirements of the calibration verification system and found to be mis-calibrated. An optical particle counter having a negative calibration status should be recalibrated.

"Pre-calibrated optical particle counter" refers to a particle counter having a positive calibration status. A pre-calibrated optical particle counter can be the same or a different particle counter as is undergoing calibration verification, or a reference optical particle counter. A pre-calibrated optical particle counter is useful as a comparison to an optical particle counter undergoing calibration verification and is also useful for providing reference calibration verification parameters. A reference optical particle counter useful as a pre-calibrated optical particle counter preferably has 100% counting efficiency at the smallest particle size of interest used in the calibration process.

"Particles" refers to small objects which are often regarded as contaminants. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1-15 µm. A particle may refer to any small object which absorbs or scatters light and is thus detectable by an optical particle counter. As used herein, "particle" is intended to be exclusive of the individual atoms or molecules of a carrier fluid, for example water molecules, oxygen molecules, helium atoms, nitrogen molecules, etc. Some embodiments of the present invention are capable of detecting, sizing, and/or counting particles comprising aggregates of material having a size greater than 50 nm, 100 nm, 1 µm or greater, or 10 µm or greater. Specific particles include particles having a size selected from 50 nm to 50 µm, a size selected from 100 nm to 10 µm, or a size selected from 500 nm to 5 µm.

"Optical communication" refers to components which are arranged in a manner that allows light or electromagnetic radiation to transfer between the components.

The terms "aerosol optical particle counter", "optical particle counter" and "particle counter" are used interchangeably herein and refer to systems capable of detecting particles suspended in a fluid, systems capable of determining the sizes of particles suspended in a fluid, systems capable of counting particles suspended in a fluid, systems capable of classification of particles suspended in a fluid, or any combination of these.

A typical liquid or aerosol optical particle counter is comprised of several components, such as a source for generating a beam of electromagnetic radiation, optics for directing the beam into a region where a fluid sample is flowing, for example a liquid or gas flowing through a flow cell. A typical optical particle counter is also comprised of a photodetector and collection optics for detecting electromagnetic radiation which is scattered off of or emitted by particles which pass through the beam, and other electronics for the processing and analysis of electrical signals produced by the photodetector including current to voltage converters and signal filtering and amplification electronics. An optical particle counter may also be comprised of a pump for creating a flow for introducing a fluid sample to the detection region where the electromagnetic beam is present.

Figure 3:
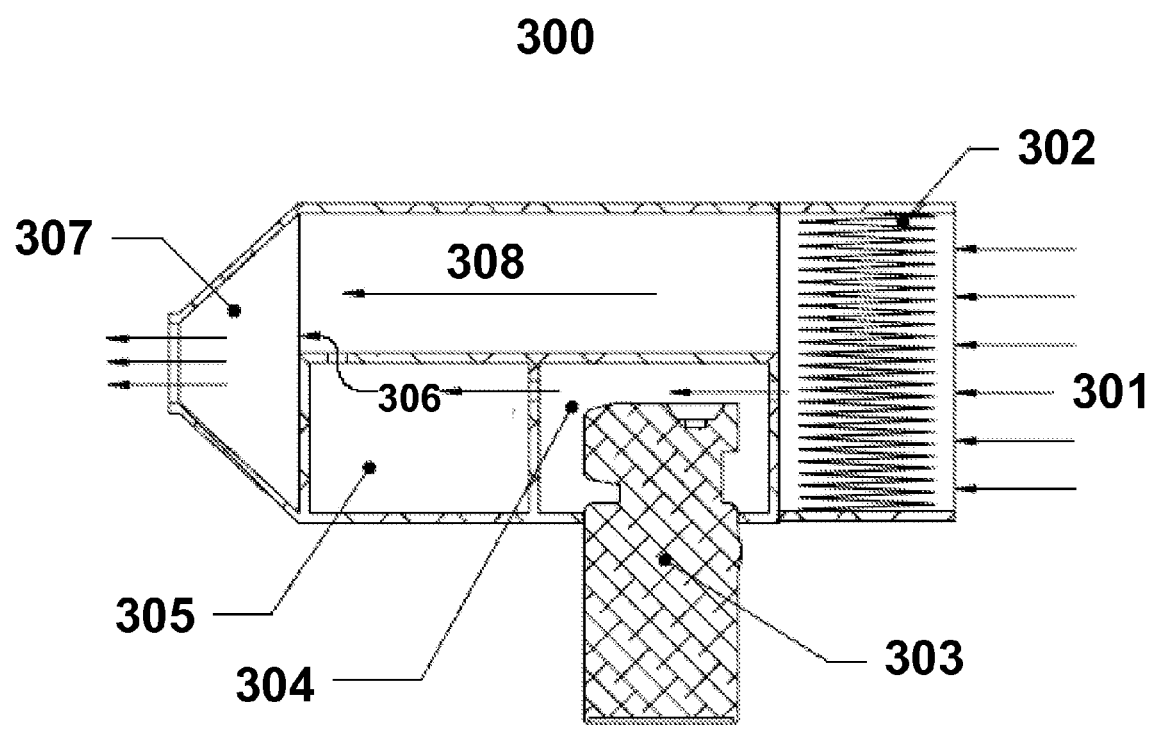
FIG. 3 illustrates a cross sectional view of a portable particle nebulization system.

In an embodiment, an optical particle counter calibration verification system comprises a particle generator. In an embodiment, a particle generator is a stable source of particles. In an embodiment, a particle generator is portable. In a specific embodiment useful with an aerosol optical particle counter, a particle generator is exemplified as a portable particle nebulization system, such as depicted in FIG. 3. In an embodiment, the particle generator generates particles having a preselected size distribution, such as a monodisperse distribution. Such particles can be formed, for example, by nebulizing a calibration standard, such as a monodisperse distribution of NIST traceable polystyrene latex spheres having a predetermined size distribution, suspended in water and allowing the water to evaporate from the resultant aerosol particles. In an embodiment, the water/particle aerosol is allowed to flow from a nebulization chamber into a drying chamber, where the water is subsequently evaporated; if desired, the particles can be diluted with filtered air, and then introduced into an optical particle counter for subsequent analysis. In a preferred embodiment, any flow required is provided by an optical particle counter; that is, the particle generator does not require a pump. In a preferred embodiment, a particle generator is also capable of providing a filtered source of fluid which is free of particles.

In a specific embodiment, the methods described herein are useful for calibration verification of a liquid particle counter. In one aspect, a particle generator useful with a liquid optical particle counter comprises a water suspension of a calibration standard, for example a monodisperse distribution of NIST traceable polystyrene latex spheres. In an embodiment, a particle generator useful with a liquid particle counter comprises a syringe, for example useful for injecting a calibration standard into the liquid particle counter. In another embodiment, a particle generator useful with a liquid particle counter comprises a pump, for example useful for introducing a calibration standard into a liquid stream introduced into a liquid particle counter. In a general embodiment, a particle generator useful with a liquid particle counter comprises a device or method for introducing particles into a liquid stream for subsequent analysis by a liquid particle counter.

In one aspect, a preferred particle generator is low powered and does not require an additional pump for generation of an aerosol. For example, the particle generator may be battery powered. In an embodiment, a particle generator useful in the present invention is a nebulizer, preferably a vibrating mesh nebulizer. In an exemplary embodiment, a particle generator useful in the present invention comprises an Omron Model NE-U22 Micro Air vibrating mesh nebulizer, which uses two AA size batteries as its power source. Having a battery power source allows such a particle generator to be especially portable and capable of being small in size. Although they may not be preferred, any particle generator is suitable for use in the particle counter calibration verification system of the present invention.

The optical particle counter calibration verification system of the present invention is also comprised of a pulse height analyzer. In an embodiment, the pulse height analyzer is an integrated component of an optical particle counter, and preferably is operably connected to a photodetector and/or the other detection and signal processing electronics in the optical particle counter. In an embodiment, the pulse height analyzer is capable of analyzing voltage pulses initially provided by a photodetector which correspond to the intensity of electromagnetic radiation scatted by particles passing through a beam of electromagnetic radiation of an optical particle counter. In an embodiment, the pulse height analyzer includes a display and displays to the user the results of the pulse height analysis as a histogram.

The optical particle counter calibration verification system of the present invention is also comprised of a calibration verification analyzer or system for the analysis of a pulse height distribution provided by the pulse height analyzer. In an embodiment, the calibration verification analyzer or system for the analysis of a pulse height distribution determines a calibration verification parameter or set of calibration verification parameters. In an embodiment, the optical particle counter calibration verification system of the present invention is comprised of a computer, hardware, or software routine capable of analyzing the pulse height distribution. In an embodiment, a calibration verification analyzer is comprised of a pulse height analyzer.

In one aspect, the analysis is performed for conditions where there are no particles in the optical particle counter; in another aspect, the analysis is performed for conditions where particles of a preselected size distribution are permitted to enter the particle counter.

In a preferred embodiment, parameters useful to the optical particle counter calibration verification system are selected from the group including, but not limited to: the median value of the pulse height distribution of particles having a preselected size distribution; the width of the pulse height distribution of particles having a preselected size distribution; the slope of the noise floor for the optical particle counter which is determined from a series of false count rates obtained when there are no particles in the optical particle counter; the zero count failure point for the optical particle counter which is determined using the slope of the noise floor for the optical particle counter; a signal-to-noise ratio for particles having a preselected size distribution, which is equal to the ratio of the median value of the pulse height distribution of the particles and the zero count failure point for the optical particle counter; and any combination of these.

In an embodiment, the optical particle counter calibration verification system is comprised of a memory system. A useful memory system is capable of storing calibration verification parameters and/or reference values. Useful reference parameters stored in such a memory system correspond to those parameters determined for an optical particle counter in a calibrated state, and preferably reference parameters previously determined for the same optical particle counter that is undergoing calibration verification.

In an embodiment, the optical particle counter calibration verification system is portable and capable of performing calibration verification on one or more optical particle counters. In a preferred embodiment, the optical particle counter calibration verification system is an integrated component of an optical particle counter. In an embodiment, the optical particle counter calibration system includes a display for indicating the calibration state of the optical particle counter to the user.

Figure 4:
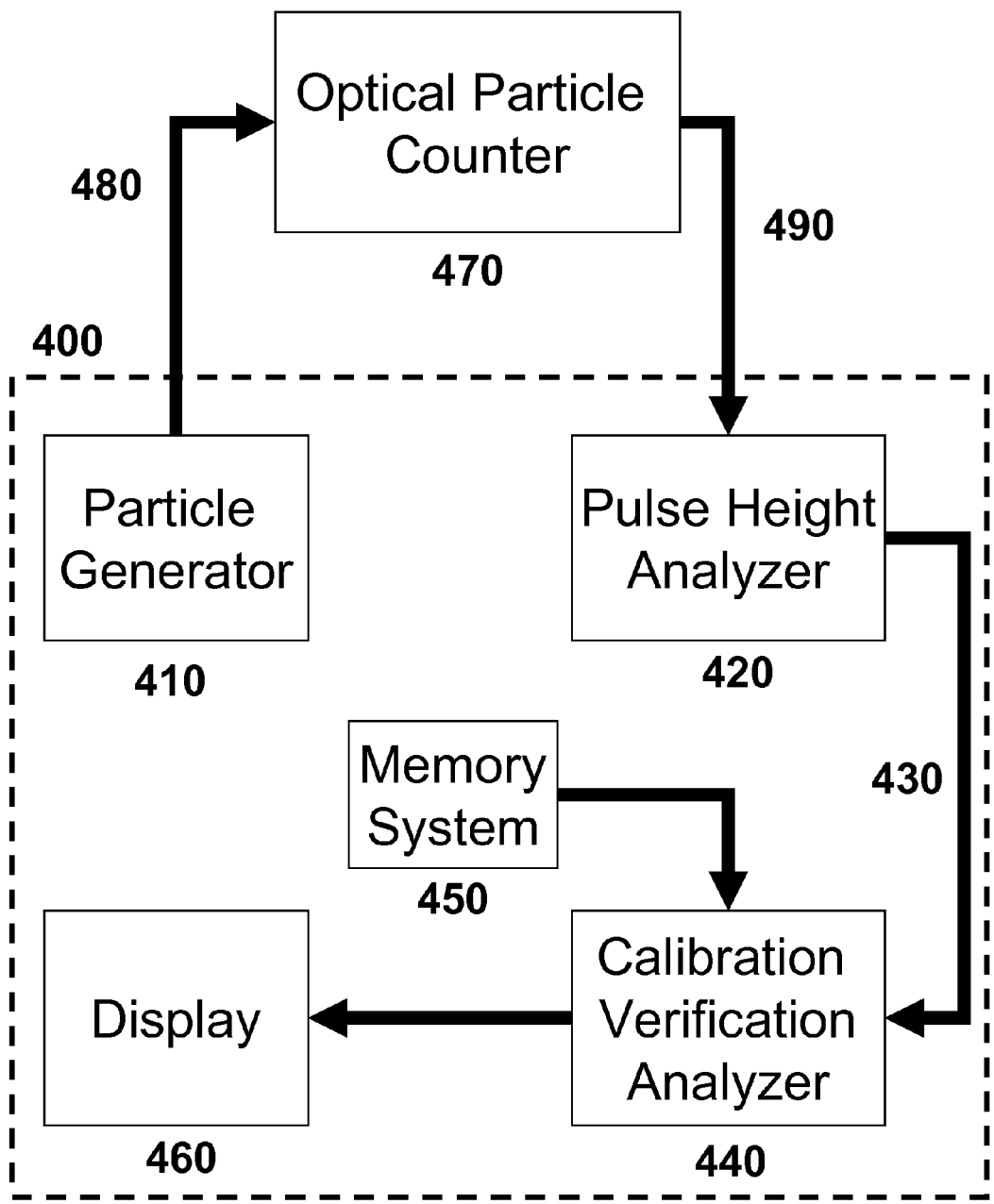
FIG. 4 illustrates an embodiment of the calibration verification system of the present invention.
Figure 5:
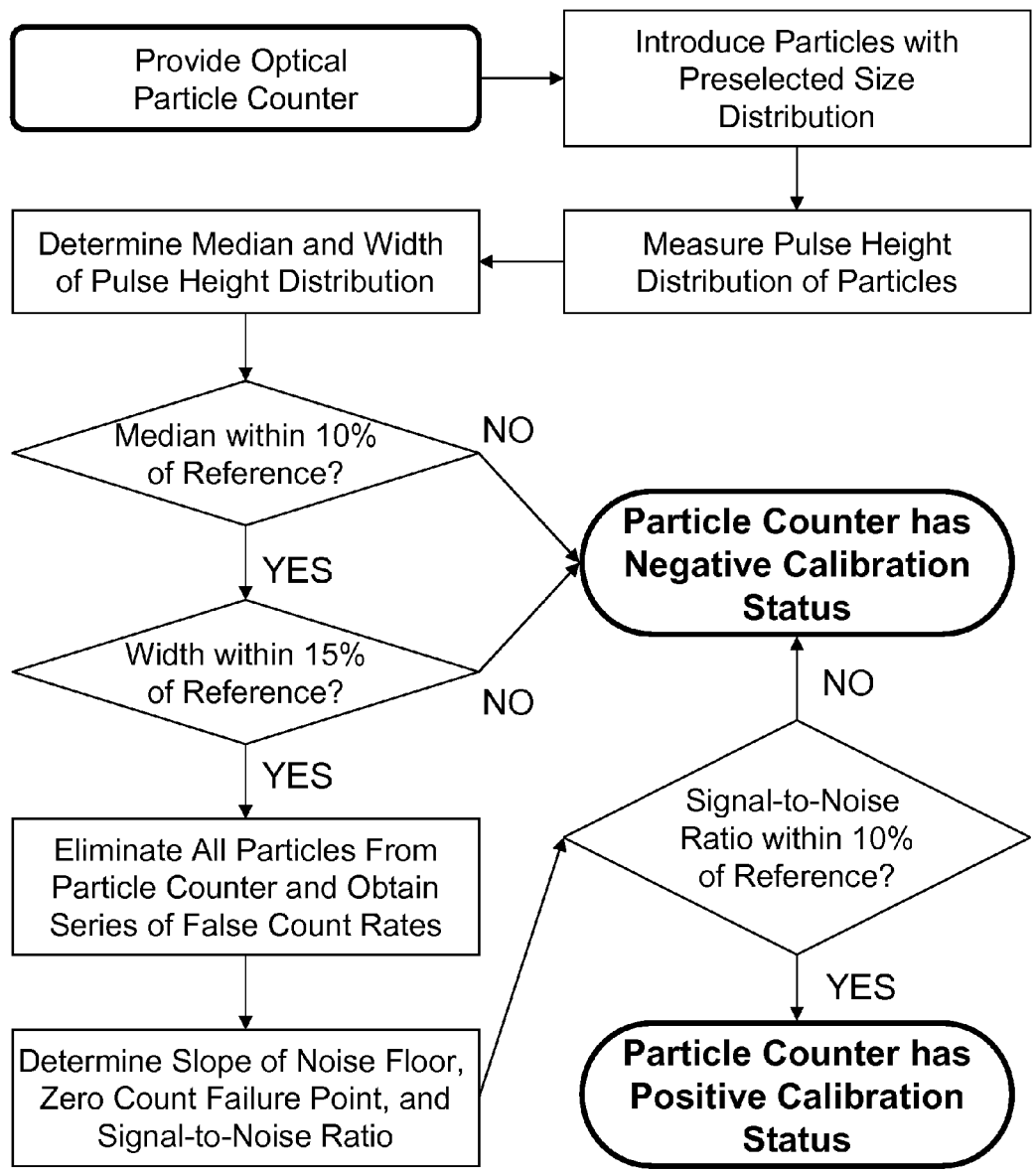
FIG. 5 illustrates an embodiment of the calibration verification method according to the present invention.

Referring now to the drawings, FIG. 4 depicts an embodiment of a calibration verification system 400 and FIG. 5 depicts an embodiment of a calibration verification method. In this embodiment, the calibration verification system 400 is comprised of a particle generator 410, a pulse height analyzer 420, a calibration verification analyzer 440, a memory system 450 and a display 460. The calibration verification system 400 is used to determine the calibration status of an optical particle counter 470 by providing a source 480 containing particles having a predetermined size distribution. The optical particle counter 470 measures and counts the sizes of the particles and provides voltage pulses 490 to the pulse height analyzer, which in turn determines the pulse height distribution 430 of the particles having the preselected size distribution. The pulse height distribution 430 is provided to the calibration verification analyzer 440, where the median and width of the pulse height distribution is determined. Reference values of a median and width of a pulse height distribution are retrieved from the memory system 450 for subsequent comparison by the calibration verification analyzer 440. If the median and width of the pulse height distribution are within 10% and 15%, respectively, of the reference median and width, then the calibration verification continues; otherwise, an indication is provided to the user on the display 460 that the optical particle counter has a negative calibration status. After the median and width of the pulse height distribution are found to be within acceptable limits of the reference values, the particle generator is switched to a mode where no particles are present in the source 480 provided to the optical particle counter 470. With no particles present in the optical particle counter 470, a series of false count rates can be determined and provided as voltage pulses 490 to the pulse height analyzer 420. The pulse height distribution 430 of the series of false count rates is provided to the calibration verification analyzer 440 which determines the slope of the noise floor and the zero count failure point of the particle counter, and subsequently the signal-to-noise ratio for the particles having the preselected size distribution. A reference value of a signal-to-noise ratio is retrieved from the memory system 450 for comparison by the calibration verification analyzer. If the signal-to-noise ratio is within 10% of the reference signal to noise ratio, then; an indication is provided to the user on the display 460 that the optical particle counter has a positive calibration status otherwise, an indication is provided to the user on the display 460 that the optical particle counter has a negative calibration status.

Statements Regarding Incorporation By Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art.

When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. One of ordinary skill in the art will appreciate that methods, device elements, starting materials, and synthetic methods other than those specifically exemplified can be employed in the practice of the invention without resorting to undue experimentation. All art-known functional equivalents of any such methods, device elements, starting materials, and synthetic methods are intended to be included in this invention. Whenever a range is given in the specification, for example, a temperature range, a time range, or a composition range, all intermediate ranges and sub-ranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention may be further understood by the following non-limiting examples.

EXAMPLE 1

Portable Particle Counter Calibration Verification System

Figure 6:
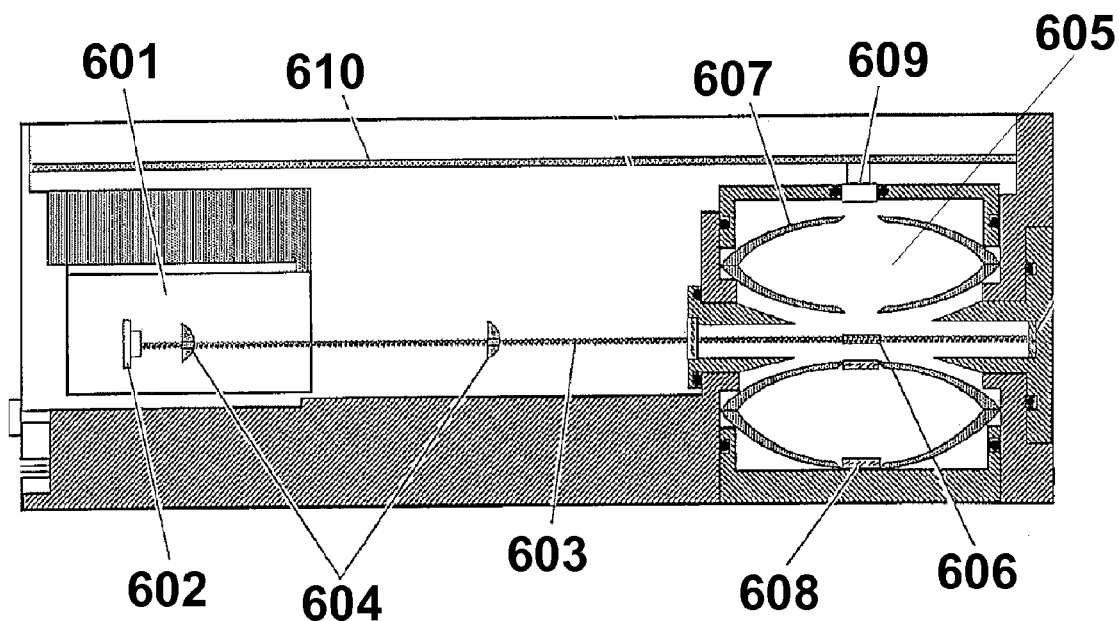
FIG. 6 illustrates the features of a typical aerosol optical particle counter.

FIG. 6 details the major design features of an aerosol optical particle counter which detects particles based on scattered electromagnetic radiation. A laser source 601 including a laser diode 602 is generally employed to generate a laser beam 603 that is then shaped and focused by beam shaping optics 604 into an optical sample chamber 605. Ambient air is drawn into the sample chamber through an inlet jet 606 by the instrument's flow system. The inlet jet 606 shapes the sample air flow in order to ensure all of the air flow is passed through the laser beam 603.

When a particle is carried into the sample chamber 605 by the sample air flow, it scatters light energy as it passes through the laser beam 603. The scattered light energy is collected by the sample chamber's collecting optics (4 mangin mirrors 607 and retro-reflector mirror 608 in the example shown in FIG. 6) and focused onto a photodiode 609.

The photodiode 609 current pulse is then converted into a voltage pulse by a current-to-voltage converter (located on a circuit board 610). The voltage pulse is then filtered and amplified by additional circuitry on the circuit board 610. Finally, the voltage pulse is then handed to a Pulse Height Analyzer (PHA).

Figure 7:
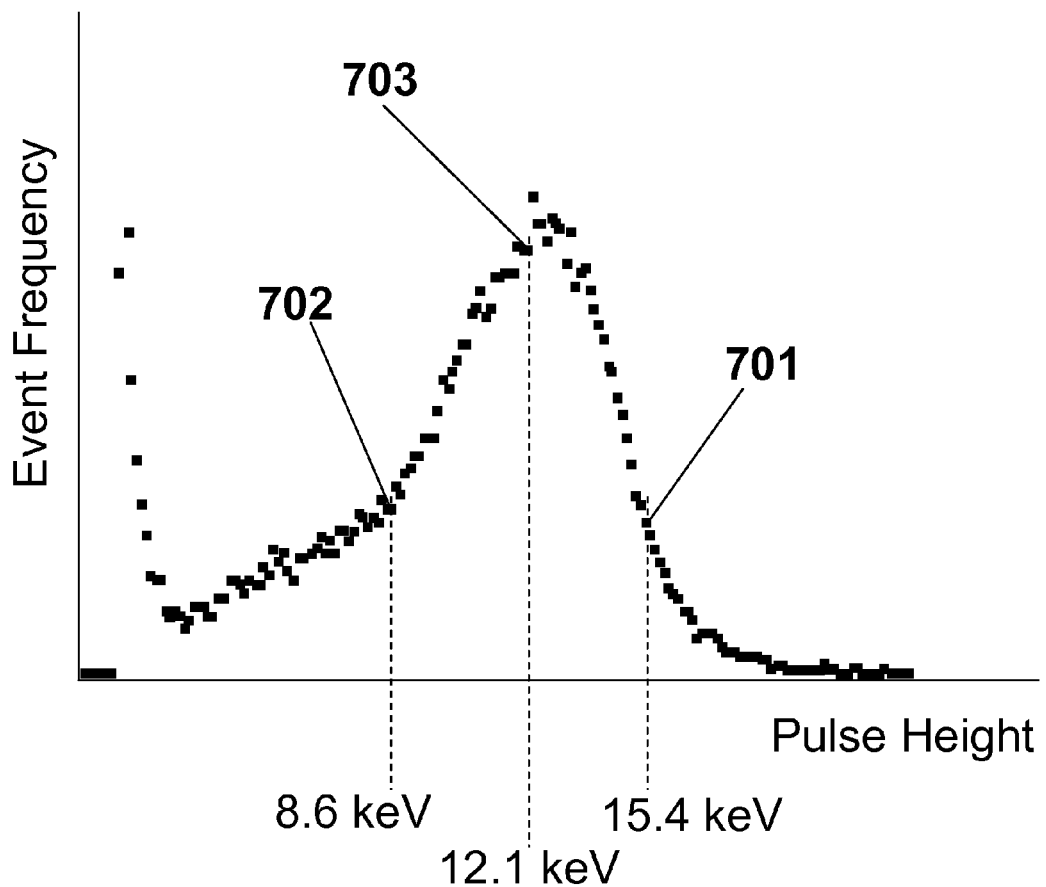
FIG. 7 illustrates an example of pulse height analyzer data.

This built-in PHA is a unique feature in a calibration verification system. FIG. 7 details the output information available from a PHA. The PHA counts particle voltage pulses. Each particle pulse is recognized and evaluated individually before being added to the population of total pulses being counted. The PHA x-axis is a range of sequential voltage bins (For example: 0-10V, from left to right). The PHA y-axis represents frequency of counted events (For example: 0-1000 particle events, from bottom to top).

The PHA measures the maximum voltage level of each particle pulse, and then places that particle event into the appropriate voltage bin. When a mono-dispersed distribution of polystyrene spheres is generated and sampled by an aerosol optical particle, a distribution similar to what is shown in FIG. 7 will be measured by the PHA. As all of the particles are similar in size, the voltage pulses will be similar in size. In an ideal situation, the particles would be exactly the same, the particle counter would measure the optical energy exactly the same for all particles, and all of the voltage pulses would be placed into a single PHA channel.

In practice, the polystyrene spheres themselves have a coefficient of variance of typically 1% to 2%. In addition, the particle counter itself will cause a widening of the distribution itself for several reasons. The laser beam typically will have variation in intensity dependent on what location in the laser beam the particle travels through. The airflow velocity across the inlet jet profile varies, and as the current-to-voltage converter may have limited bandwidth, the particle pulses will vary in amplitude due to differences in velocity. The collecting optics have practical limits to their ability to collect light without blurring images off of the photodiode and will therefore also cause variation in particle pulse amplitude dependent on the particles relative position to the optical system when it passes through the laser beam.

All of these reasons will cause a spread in the particle distribution from ideal. In terms of particle size, 10% is a typical resolution measurement for an optical particle counter, and looks quite similar to the PHA distribution shown in FIG. 7.

Two very important measurements can be taken from the mono-dispersed particle distribution generated from a particle counter. The first is the median voltage of the distribution. This is the voltage that the particle counter channel size should be calibrated to. For example: if the particle counter has a 0.5 μm channel, that channel size voltage should be calibrated to be equal to the median value of a 0.5 μm mono-dispersed distribution of a certified particle size standard. If this median voltage for a channel size is stored in the particle counters memory when it is calibrated, that particle size can be tested at a later time to ensure that it continues to produce a distribution with a median voltage that is similar to the original stored calibration value.

The second important measurement that can be taken from the mono-dispersed particle distribution PHA data is the width of the particle distribution. As an example, the width of the distribution can be defined as the upper 701 and lower 702 limits (as represented by a voltage value for each limit) of the particle distribution. Here, the upper 701 and lower 702 limits are determined by defining a specific fall off in event activity as compared to the median 703 of the distribution. The measurement represents the resolution of the particle counter, and can be stored in memory when the particle counter is calibrated. If this resolution measurement for a particle size is stored in the particle counters memory when it is calibrated, that particle size can be tested at a later time to ensure that it continues to produce a resolution measurement value that is similar to the original stored calibration value.

A third important measurement that can be taken is the slope of the noise floor of the system. The PHA x-axis (a range of sequential voltage bins) channels can be distributed into the peak noise of the particle counter. The y-axis is a series of sequential counts (frequency) bins. This voltage-vs.-counts data is a measurement of the particle counter's false count rate at different voltage threshold levels and can be expressed as counts per second (counts/sec). In an embodiment, the industry standard zero-count requirement for an aerosol particle counter of less than one count in five minutes can be calculated as 0.00333 counts per second. Once the false count rate is determined at several different voltage levels, the data can be plotted, similar to an example shown in FIG. 8.

Figure 8:
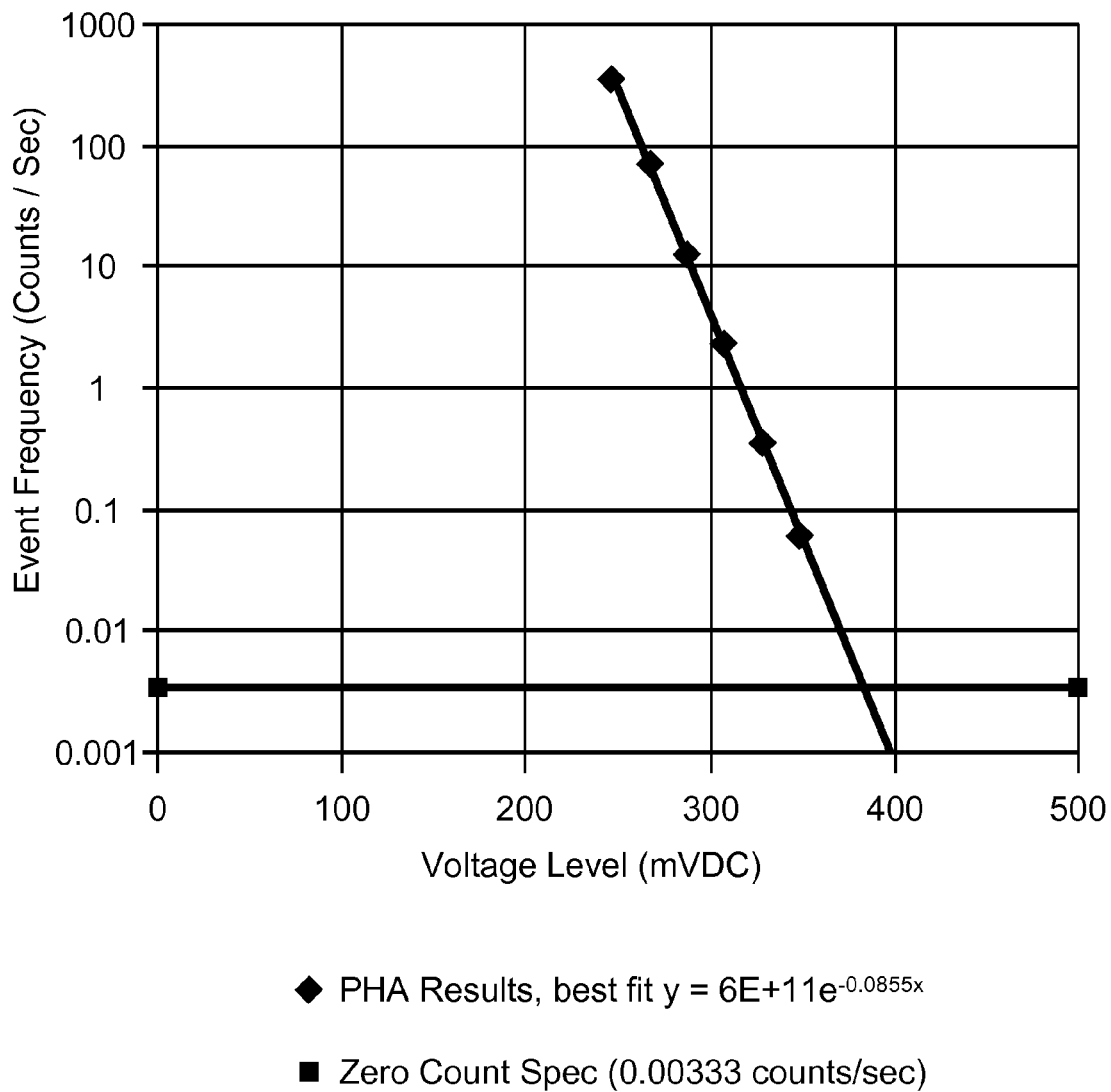
FIG. 8 illustrates an example of a pulse height analyzer false count rate test result.

The zero-count failure point (380 mV dc in the example of FIG. 8) can be determined by fitting a line to the known data points and extrapolating out to the actual predicted failure point, exemplified as 0.00333 counts per second. When shown on a log-linear graph the line should appear as a straight line (as shown in FIG. 8). The ratio of this predicted zero-count failure point to the median of a particle counter's median channel for a mono-dispersed particle distribution (discussed earlier) is the particle counter's signal to noise ratio and is an excellent measure of the particle counter's relative health.

While this measurement is not as thorough as a full zero-count test, it is a good indicator of a particle counter's ability to zero-count and can be accomplished in a several minute test rather than the extended period of time an actual zero-count test would require. This measurement is also capable of detecting deterioration in system performance that may not yet be detectable in the extended zero-count test. If this signal to noise ratio measurement is stored in the particle counter's memory when it is calibrated, the signal to noise ratio can be tested at a later time to ensure that it continues to produce a measurement value that is similar to the original stored calibration value.

A particle counter that has the ability to store in memory these three critical measurements explained above, has the ability to a large extent, to perform a self-calibration verification check at a later time. Almost all circumstances that can cause a particle counter to drift out of calibration will cause a measurable difference in either or both of the median voltage measurement and resolution measurement of a test particle. Any significant increase in the system noise level would be detectable by a signal to noise ratio verification test.

A change in laser beam power, laser beam intensity, loss of collecting optic efficiency (for example: due to collecting optic contamination), or a failure of the related electronic circuitry will all cause a change in the median voltage measurement. A significant change in laser beam shape, laser beam position, inlet jet position, inlet jet flow profile (May be altered by an obstruction in the inlet jet), and collecting optics position and/or relative health (Damage) will all cause a change in the resolution measurement of the test particle.

Figure 9:
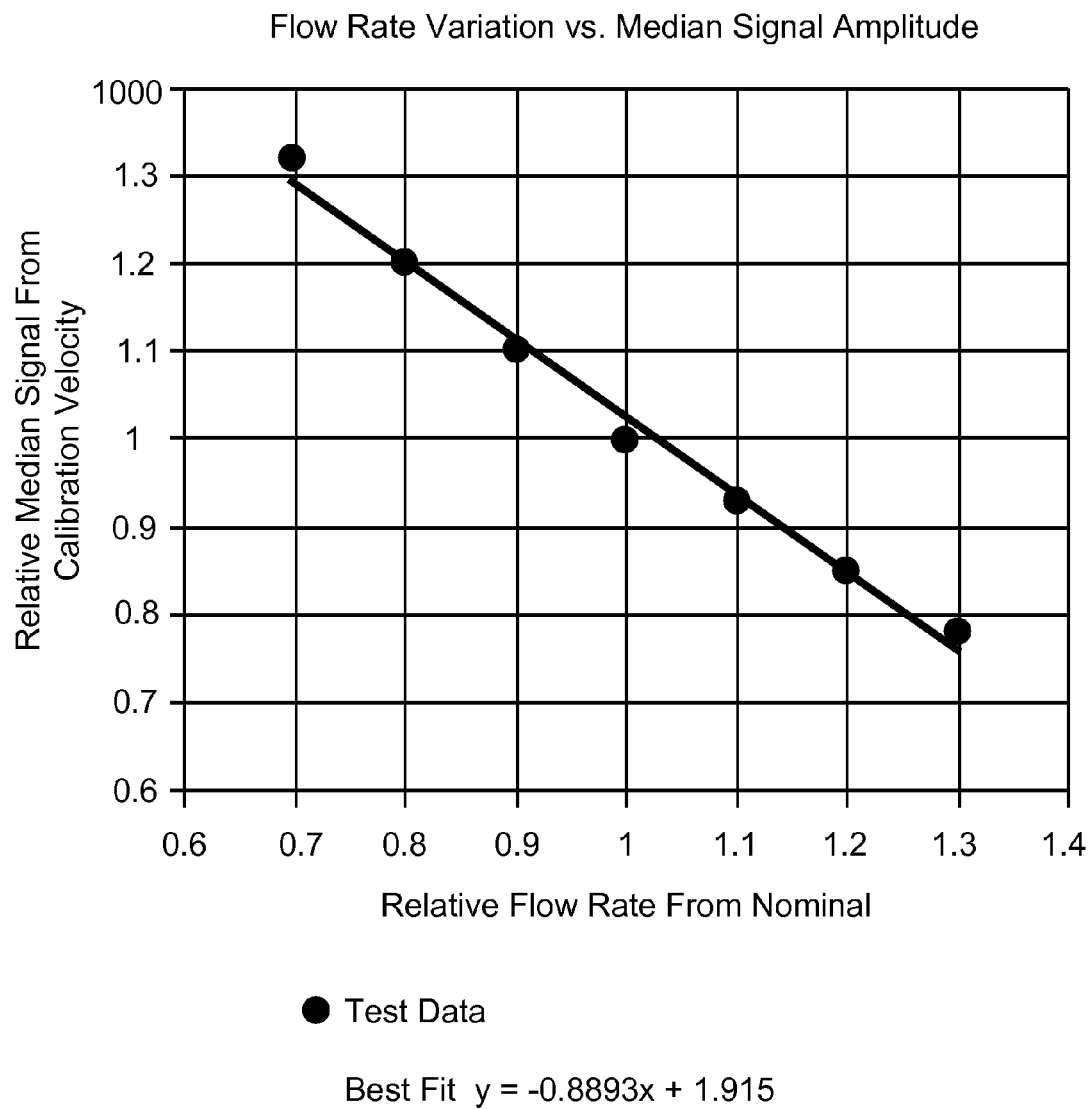
FIG. 9 illustrates data showing the relationship between flow rate and median signal amplitude.

A mechanism for detecting a major error in instrument flow rate is also needed. The median voltage measurement can to a large extent be used for this purpose. A significant change in particle velocity, due to a change in instrument flow rate, will cause a change in the median voltage measurement. This is due to bandwidth limitations of the electronic circuitry, particularly of the current-to-voltage converter circuit. As is shown in FIG. 9, there is essentially an inverse linear relationship between instrument flow rate and median signal strength for modest (±30%) deviations in instrument flow rate from nominal.

A 10% decrease in instrument flow rate will cause approximately a 10% increase in median signal strength. Therefore it is possible to establish that there is no significant deviation in instrument flow rate if there is no significant deviation in the median signal amplitude.

Any significant increase in the particle counter's noise level has the potential to induce noise related counts that will elevate the instrument's reported particle count levels. The noise level may be related to an increase in laser intensity, an electronic component failure, critical contamination in the optical block, or an actual fluidic leak in the optical block (particles entering the particle counter through a path other than the inlet jet). A signal to noise ratio verification test can quickly and easily ensure that this has not happened.

These three measurements of are the key factors in determining the relative health and calibration accuracy of an aerosol optical particle counter. What is needed is a system for easily delivering the mono-dispersed test particle to the particle counter. The system should be portable so that the test may be performed at the location of any particle counter. The system should be cordless, to eliminate the need for available AC power at the location of the particle counter. The system should be small and light weight to make it easily portable from one location to another. The system should be quick and simple for a particle counter user to run. Shown in FIG. 3 is such a system; a portable particle nebulization system 300. Ambient air 301 is drawn into nebulization system 300 through a filter 302 to generate a filtered air flow.

The portable particle nebulization system utilizes an Omron Model NE-U22 Micro-Air vibrating mesh nebulizer 303 to aerosolize the polystyrene particle and water mixture that is placed by the user into the nebulizer 303. The Micro-Air nebulizer does not require the air pump used in tradition particle generation systems. Because there is no pump, the power requirements for this system are minimal. The nebulizer 303 can run for many hours on two AA size batteries. All air flows that are required in the system are drawn through the nebulization system 300 by the particle counter that is being tested.

Once the water/particle mixture is nebulized into the nebulization chamber 304, a small filtered air flow pulls a controlled amount out of the nebulization chamber 304 and into the drying chamber 305. Once in the drying chamber 305, the water droplets are allowed to evaporate and only the polystyrene spheres then remain in the air flow. The particle air flow 306 is then mixed in mixing chamber 307 with the filtered bypass air flow 308 and then pulled into the particle counter that is being tested.

The device may also be used to provide filtered air to the particle counter while the counter's noise floor is being measured for a signal to noise ratio measurement. This device meets all of the requirements for a portable system that quickly and easily delivers mono-dispersed test particles and filtered air to the particle counter.

REFERENCES

Omron—Instruction Manual—Micro Air Vibrating Mesh Nebulizer Models NE-U22V and NE-U22VAC.

JIS B 9921: Light Scattering Automatic Particle Counter.

ASTM F328-98: Standard Practice for Calibrating an Airborne Particle Counter Using Monodisperse Spherical Particles ISO/FDIS 21501-4 Determination of particle size distribution—Single particle light interaction methods—Part 4: Light scattering airborne particle counter for clean spaces.

We claim:

1. A calibration verification system for verifying the calibration status of an optical particle counter comprising:
    a particle generator for providing particles having a predetermined size distribution to an optical particle counter;
    a pulse height analyzer operably connected to said optical particle counter for measuring a pulse height distribution for said particles having said predetermined size distribution; and
    a calibration verification analyzer operably connected to said pulse height analyzer for analyzing said pulse height distribution by:
        receiving said pulse height distribution for said particles having said predetermined size distribution from said pulse height analyzer;
        determining a calibration verification parameter or set of calibration verification parameters from said pulse height distribution for said particles having said predetermined size distribution;
        wherein said calibration verification parameters are selected from the group consisting of:
            a median value of said pulse height distribution for said particles having said predetermined size distribution;
            a width of said pulse height distribution for said particles having said predetermined size distribution;
            a slope of the noise floor for said optical particle counter;
            a zero count failure point for said optical particle counter; and
            a signal-to-noise ratio equal to the ratio of said median value of said pulse height distribution for said particles having said predetermined size distribution and said zero count failure point for said optical particle counter; and
        comparing said calibration verification parameter or set of calibration verification parameters with one or more reference values;
        wherein said calibration verification system is an integrated component of said optical particle counter.

2. The calibration verification system of claim 1, wherein said particle generator comprises a nebulizer.

3. The calibration verification system of claim 2, wherein said nebulizer is a vibrating mesh nebulizer.

4. The calibration verification system of claim 1, wherein said one or more reference values are selected from the group consisting of:
    a median value of a pulse height distribution for particles having said predetermined size distribution for a pre-calibrated optical particle counter;
    a width of a pulse height distribution for particles having said predetermined size distribution for a pre-calibrated optical particle counter;
    a slope of the noise floor for a pre-calibrated optical particle counter;
    a zero count failure point for a pre-calibrated optical particle counter; and
    a signal-to-noise ratio equal to the ratio of said median value of said pulse height distribution for particles having said predetermined size distribution for a pre-calibrated optical particle counter and a zero count failure point determined using said slope of the noise floor for a pre-calibrated optical particle.

5. The calibration verification system of claim 1 further comprising a memory system for storing said calibration verification parameters, said one or more reference values, or both said calibration verification parameters and said one or more reference values.

6. The calibration verification system of claim 1, wherein said optical particle counter is an aerosol optical particle counter.

7. The calibration verification system of claim 1, wherein said predetermined size distribution comprises a monodisperse size distribution.

8. The calibration verification system of claim 7, wherein said predetermined size distribution comprises a plurality of monodisperse size distributions.

9. The calibration system of claim 1, wherein a standard deviation of said predetermined size distribution is known.

10. The calibration system of claim 1, wherein a median of said predetermined size distribution is known.

11. The calibration system of claim 1, wherein said predetermined size distribution of particles comprises calibration standard particles.

12. A method for verifying the calibration status of an optical particle counter, said method comprising:
    providing an optical particle counter having a calibration verification system, wherein said calibration verification system is an integrated component of said optical particle counter;
    transporting particles having a predetermined size distribution through said optical particle counter;
    measuring a pulse height distribution corresponding to said particles having said predetermined size distribution;
    analyzing said pulse height distribution by determining a calibration verification parameter or set of calibration verification parameters from said pulse height distribution for said particles having said predetermined size distribution;
    wherein said calibration verification parameters are selected from the group consisting of:

a median value of said pulse height distribution for said particles having said predetermined size distribution;
a width of said pulse height distribution for said particles having said predetermined size distribution;
a slope of the noise floor for said optical particle counter;
a zero count failure point for said optical particle counter; and
a signal-to-noise ratio equal to the ratio of said median value of said pulse height distribution for said particles having said predetermined size distribution and said zero count failure point for said optical particle counter; and
comparing said calibration verification parameter or set of calibration verification parameters with one or more reference values, thereby verifying the calibration status of an optical particle counter.

13. The method of claim 12 further comprising the step of indicating the calibration status of said optical particle counter to a user.

14. The method of claim 12 further comprising the step of storing said calibration verification parameter or said set of calibration verification parameters in a memory system of the optical particle counter.

15. The method of claim 12, wherein said one or more reference values are selected from the group consisting of:
a median value of a pulse height distribution for particles having said preselected predetermined size distribution for said pre-calibrated optical particle counter;
a width of a pulse height distribution for particles having said predetermined size distribution for said pre-calibrated optical particle counter;
a slope of the noise floor for said pre-calibrated optical particle counter;
a zero count failure point for said pre-calibrated optical particle counter;
a signal-to-noise ratio equal to the ratio of said median value of said pulse height distribution for particles having said predetermined size distribution for said pre-calibrated optical particle counter and a zero count failure point for said pre-calibrated optical particle counter.

16. The method of claim 12, wherein said comparing step comprises comparing the median value of said pulse height distribution for said optical particle counter with the median value of a pulse height distribution for particles having said predetermined size distribution for said pre-calibrated optical particle counter; said method further comprising the steps of:
indicating a positive calibration status of said optical particle counter if the median value of said pulse height distribution for said optical particle counter is within 10% of the median value of said pulse height distribution for said pre-calibrated optical particle counter; and
indicating a negative calibration status of said optical particle counter if the median value of said pulse height distribution for said optical particle counter is greater than 110% or less than 90% of the median value of said pulse height distribution for said pre-calibrated optical particle counter.

17. The method of claim 12, wherein said comparing step comprises comparing the width of said pulse height distribution for said optical particle counter with the width of a pulse height distribution for particles having said predetermined size distribution for said pre-calibrated optical particle counter; said method further comprising the steps of:
indicating a positive calibration status of said optical particle counter if the width of said pulse height distribution for said optical particle counter is within 15% of the width of said pulse height distribution for said pre-calibrated optical particle counter; and
indicating a negative calibration status of said optical particle counter if the width of said pulse height distribution for said optical particle counter is greater than 115% or less than 85% of the width of said pulse height distribution for said pre-calibrated optical particle counter.

18. The method of claim 12, wherein said comparing step comprises comparing a slope of the noise floor for said optical particle counter with a slope of the noise floor for said pre-calibrated optical particle counter; said method further comprising the steps of:
indicating a positive calibration status of said optical particle counter if the slope of the noise floor for said optical particle counter is within 10% of the slope of the noise floor for the pre-calibrated optical particle counter; and
indicating a negative calibration status of said optical particle counter if the slope of the noise floor for said optical particle counter is greater than 110% or less than 90% of the slope of the noise floor for said pre-calibrated optical particle counter.

19. The method of claim 12, wherein said comparing step comprises comparing a zero count failure point for said optical particle counter with a zero count failure point for said pre-calibrated optical particle counter; said method further comprising the steps of:
indicating a positive calibration status of said optical particle counter if the zero count failure point for said optical particle counter is within 10% of the zero count failure point for the pre-calibrated optical particle counter; and
indicating a negative calibration status of said optical particle counter if the zero count failure point for said optical particle counter is greater than 110% or less than 90% of the zero count failure point for said pre-calibrated optical particle counter.

20. The method of claim 12, wherein said comparing step comprises comparing the signal-to-noise ratio for said optical particle counter with a signal-to-noise ratio for said pre-calibrated optical particle; said method further comprising the steps of:
indicating a positive calibration status of said optical particle counter if the signal-to-noise ratio for said optical particle counter is within 10% of the signal-to-noise ratio for said pre-calibrated optical particle counter; and
indicating a negative calibration status of said optical particle counter if the signal-to-noise ratio for said optical particle counter is greater than 110% or less than 90% of the signal-to-noise ratio for said pre-calibrated optical particle counter.

21. The method of claim 12, wherein said predetermined size distribution comprises a monodisperse size distribution.

22. The method of claim 21, wherein said predetermined size distribution comprises a plurality of monodisperse size distributions.

23. The calibration system of claim 12, wherein a standard deviation of said predetermined size distribution is known.

24. The calibration system of claim 12, wherein a median of said predetermined size distribution is known.

25. The calibration system of claim 12, wherein said predetermined size distribution of particles comprises calibration standard particles.

26. An optical particle counter comprising:
a source for generating a beam of electromagnetic radiation;

a particle generator for generating particles having a predetermined size distribution that are transported through said beam; thereby generating electromagnetic radiation scattered by said particles;

a photodetector for detecting said electromagnetic radiation scattered by said particles and generating output signals corresponding to intensities of said electromagnetic radiation scattered by said particles;

an integrated pulse height analyzer operably connected to said photodetector, wherein said pulse height analyzer receives said output signals from said photodetector and measures a pulse height distribution for said particles having said predetermined size distribution; and a calibration verification analyzer operably connected to said pulse height analyzer for analyzing said pulse height distribution by determining a calibration verification parameter or set of calibration verification parameters from said pulse height distribution for said particles having said predetermined size distribution and comparing said calibration verification parameter or set of calibration verification parameters with one or more reference values:

wherein said calibration verification parameters are selected from the group consisting of:
   a median value of said pulse height distribution for said particles having said predetermined size distribution;
   a width of said pulse height distribution for said particles having said predetermined size distribution;
   a slope of the noise floor for said optical particle counter;
   a zero count failure point for said optical particle counter; and
   a signal-to-noise ratio equal to the ratio of said median value of said pulse height distribution for said particles having said predetermined size distribution and said zero count failure point for said optical particle counter.

27. The optical particle counter of claim 26, wherein said one or more reference values are selected from the group consisting of:
   a median value of a pulse height distribution for particles having said preselected predetermined size distribution for a pre-calibrated optical particle counter;
   a width of a pulse height distribution for particles having said preselected predetermined size distribution for a pre-calibrated optical particle counter;
   a slope of the noise floor for a pre-calibrated optical particle counter;
   a zero count failure point for a pre-calibrated optical particle counter; and
   a signal-to-noise ratio equal to the ratio of said median value of said pulse height distribution for particles having said preselected predetermined size distribution for a pre-calibrated optical particle counter and a zero count failure point determined using said slope of the noise floor for a pre-calibrated optical particle counter.

28. The optical particle counter of claim 26, wherein said particle generator is a nebulizer.

29. The optical particle counter of claim 28, wherein said nebulizer is a vibrating mesh nebulizer.

30. The optical particle counter of claim 26 further comprising a memory storing system for storing said calibration verification parameters and said one or more reference values.

31. The optical particle counter of claim 26 further comprising a flow cell for transporting said particle through said beam of electromagnetic radiation, said flow cell provided in optical communication with said optical source.

32. The optical particle counter of claim 26, wherein said optical particle counter is an aerosol optical particle counter.

33. The optical particle counter of claim 26, wherein said optical particle counter is a liquid particle counter.

34. The optical particle counter of claim 26, wherein said predetermined size distribution comprises a monodisperse size distribution.

35. The optical particle counter of claim 34, wherein said predetermined size distribution comprises a plurality of monodisperse size distributions.

36. The calibration system of claim 26, wherein a standard deviation of said predetermined size distribution is known.

37. The calibration system of claim 26, wherein a median of said predetermined size distribution is known.

38. The calibration system of claim 26, wherein said predetermined size distribution of particles comprises calibration standard particles.

* * * * *

UNITED STATES PATENT AND TRADEMARK OFFICE
CERTIFICATE OF CORRECTION

| | | |
|---|---|---|
| PATENT NO. | : 7,973,929 B2 | Page 1 of 1 |
| APPLICATION NO. | : 12/271565 | |
| DATED | : July 5, 2011 | |
| INVENTOR(S) | : Thomas Bates | |

It is certified that error appears in the above-identified patent and that said Letters Patent is hereby corrected as shown below:

In claim 15, column 19, line 28, please replace "having said preselected predetermined size distribution" with -- having said predetermined size distribution --

In claim 27, column 21, line 42, please replace "having said preselected predetermined size distribution" with -- having said predetermined size distribution --

In claim 27, column 22, line 2, please replace "said preselected predetermined size distribution for a" with -- said predetermined size distribution for a --

In claim 27, column 22, line 10, please replace "having said preselected predetermined size distribution for a" with -- having said predetermined size distribution for a --

Signed and Sealed this
Eighth Day of November, 2011

David J. Kappos
*Director of the United States Patent and Trademark Office*